US010633623B2

(12) United States Patent
Huh et al.

(10) Patent No.: US 10,633,623 B2
(45) Date of Patent: Apr. 28, 2020

(54) ARTIFICIAL PLACENTA AND METHODS OF PREPARATION

(71) Applicant: THE TRUSTEES OF THE UNIVERSITY OF PENNSYLVANIA, Philadelphia, PA (US)

(72) Inventors: Dongeun Huh, Villanova, PA (US); Cassidy Blundell, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 66 days.

(21) Appl. No.: 15/559,758

(22) PCT Filed: Mar. 23, 2016

(86) PCT No.: PCT/US2016/023790
§ 371 (c)(1),
(2) Date: Sep. 19, 2017

(87) PCT Pub. No.: WO2016/154319
PCT Pub. Date: Sep. 29, 2016

(65) Prior Publication Data
US 2018/0044623 A1 Feb. 15, 2018

Related U.S. Application Data

(60) Provisional application No. 62/137,602, filed on Mar. 24, 2015.

(51) Int. Cl.
C12M 3/06 (2006.01)
C12M 1/12 (2006.01)
C12M 1/42 (2006.01)
B81C 1/00 (2006.01)
B81B 7/00 (2006.01)
(Continued)

(52) U.S. Cl.
CPC ........... *C12M 23/16* (2013.01); *B01D 63/088* (2013.01); *B81B 3/00* (2013.01); *B81B 7/00* (2013.01); *B81C 1/00* (2013.01); *C12M 25/02* (2013.01); *C12M 35/08* (2013.01); *C12M 41/30* (2013.01); *G01N 33/5005* (2013.01)

(58) Field of Classification Search
None
See application file for complete search history.

(56) References Cited

U.S. PATENT DOCUMENTS 7,960,166 B2 * 6/2011 Vacanti ............... C12N 5/0062
435/1.1
2014/0147880 A1 5/2014 Ingber et al.

OTHER PUBLICATIONS

ATCC Cell line information "HTR-8/SVneo" retrieved from https://www.atcc.org/Products/All/CRL-3271.aspx?&p=1&rel=characteristics#characteristics on Dec. 18, 2019 (Year: 2019).*
(Continued)

Primary Examiner — Allison M Fox
(74) Attorney, Agent, or Firm — Baker Botts L.L.P.

(57) ABSTRACT

The presently disclosed subject matter provides a microfluidic device that can simulate capillary blood flow on a fetal side of the device and pooled blood on a maternal side of the device (i.e., intervillous space). The microfluidic device can reconstitute the maternal-fetal interface, can expand the capabilities of cell culture models, and can provide an alternative to current maternal-fetal transfer models.

18 Claims, 10 Drawing Sheets

(51) Int. Cl.
  B81B 3/00      (2006.01)
  B01D 63/08     (2006.01)
  C12M 1/34      (2006.01)
  G01N 33/50     (2006.01)

(56) References Cited

OTHER PUBLICATIONS

Huh et al, "Reconstituting Organ-Level Lung Functions on a Chip" Science, 2010, vol. 328, Issue 5986, pp. 1662-1668. (Year: 2010).*

Levkovitz et al "In vitro simulation of placental transport: Part I. Biological model of the placental barrier." Placenta, 2013, vol. 34, pp. 699-707. (Year: 2013).*

Blundell et al., "A microphysiological model of the human placental barrier," Lab on a Chip 16:3065-3073 (2016).

Blundell et al., "Placental Drug Transport-on-a-Chip: A Microengineered In Vitro Model of Transporter-Mediated Drug Efflux in the Human Placental Barrier," Advanced Healthcare Materials, 7:1700786 (2018), 9 pages.

Extended European Search Report dated Nov. 20, 2018 in Application No. EP 16769614.

Lee et al., "Placenta-on-a-chip: a novel platform to study the biology of the human placenta," Journal Matern Fetal Neonatal Med, 29(7):1046-1054 (2016).

Miura et al., "Multi-layered placental barrier structure integrated with microfluidic channels," MEMS 2013, Taipei, Taiwan, Jan. 20-24, 2013, pp. 257-258.

Bhatia et al., "Microfluidic organs-on-chips," Nat Biotechnol. 32(8):760-772 (2014).

Heaton et al., "The use of BeWo cells as an in vitro model for placental iron transport," Am J. Physiol Cell Physiol. 295(5):C1445-C1453 (2008).

Huh et al., "Microfabrication of human organs-on-chips," Nature Protocols 8(11):2135-2157 (2013).

International Search Report dated Jun. 27, 2016 in International Application No. PCT/US2016/023790.

Qing et al., "Red Blood Cells Induce Necroptosis of Lung Endothelial Cells and Increase Susceptibility to Lung Inflammation," Am J Respir Crit Care Med. 190(11):1243-1254 (2014).

Su et al., "Estrogen receptor-beta mediates cyclooxygenase-2 expression and vascular prostanoid levels in human placental villous endothelial cells," Am J Obstet Gynecol. 200:427.e1-427.e8 (2009).

Thuenauer et al., "Microfluidic approaches for epithelial cell layer culture and characterization," Analyst 139(13):3206-3218 (2014).

Wang et al., "Live Cell Imaging of In Vitro Human Trophoblast Syncytialization," Biol Reprod. 90(6):117, 1-10 (2014).

* cited by examiner

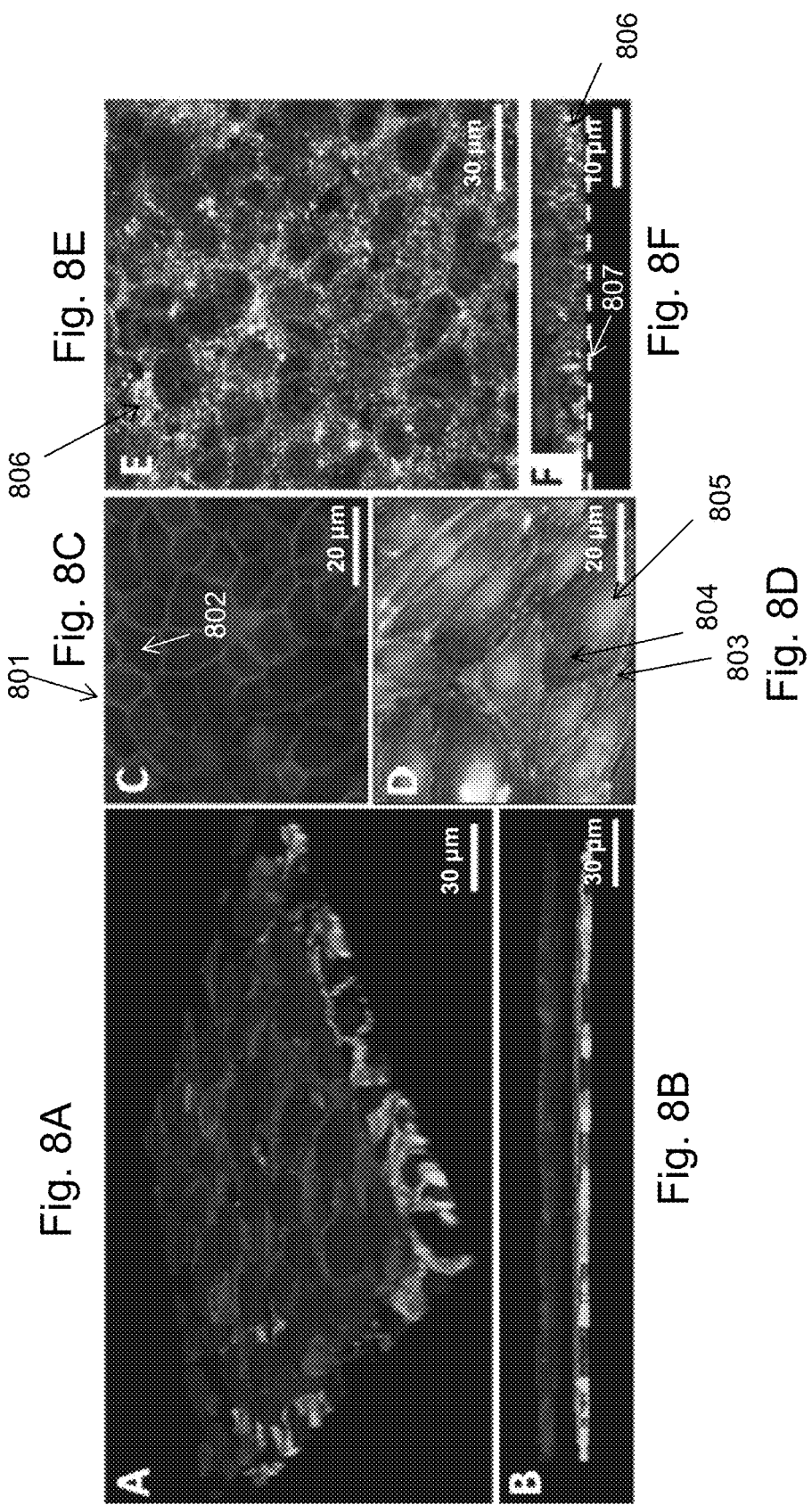

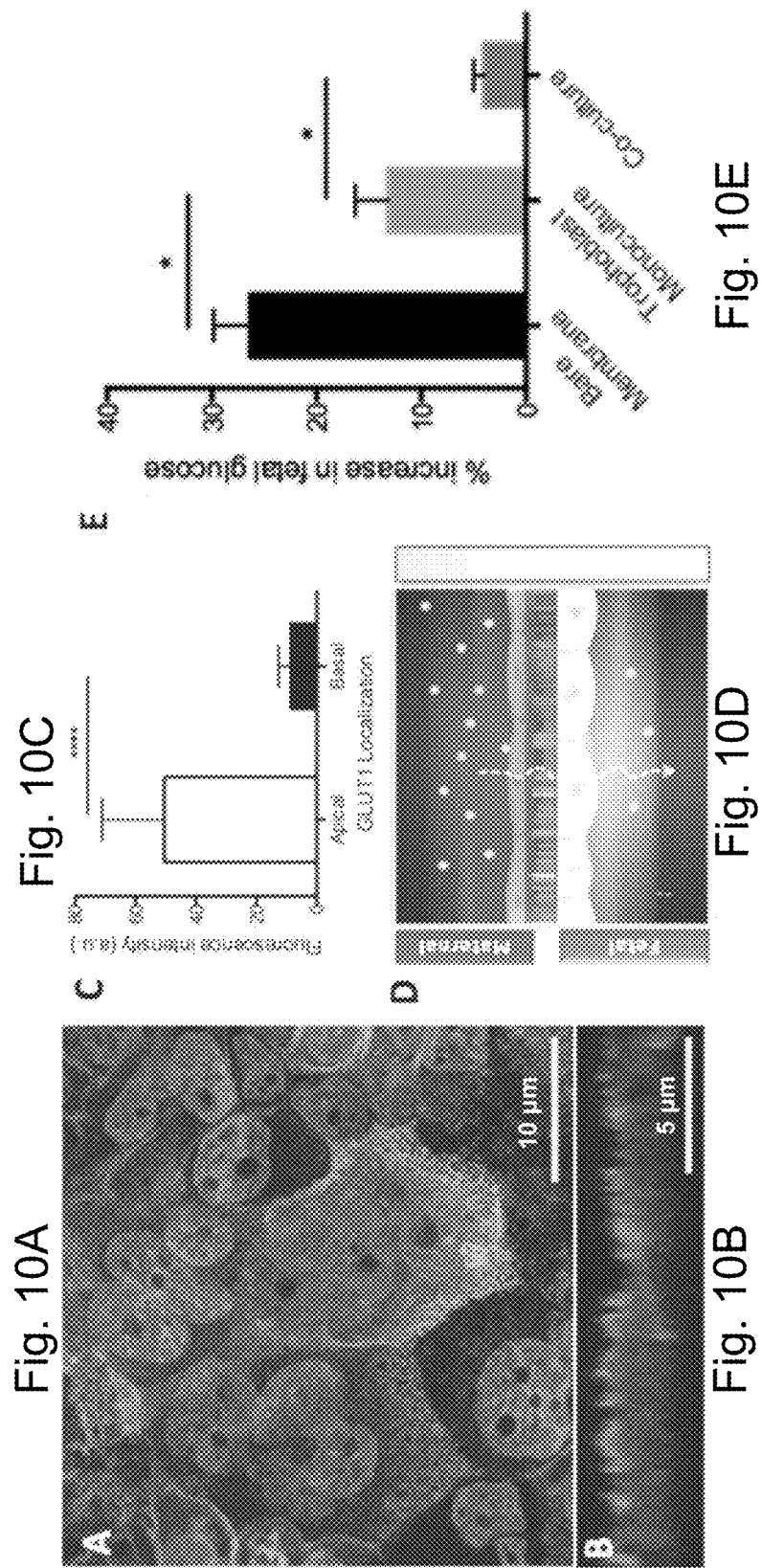

ARTIFICIAL PLACENTA AND METHODS OF PREPARATION

CROSS-REFERENCE TO RELATED APPLICATIONS

This application is a U.S. National Stage Patent Application under 35 U.S.C. § 371 of International Application No. PCT/US2016/023790 filed on Mar. 23, 2016, which claims priority to U.S. Provisional Application Ser. No. 62/137,602 filed on Mar. 24, 2015, which are both incorporated by reference herein in their entireties and from which priority is claimed.

BACKGROUND

The placenta plays an important role in the development and maintenance of pregnancy, as well as fetal growth and health. During pregnancy, the thin tissue layer that separates the maternal and fetal circulations is known as the placental barrier. This maternal-fetal interface in the human placenta regulates the exchange of nutrients, gases, metabolic waste, and xenobiotics between the intervillous space and fetal capillaries. In particular, in the chorionic villi of third trimester placenta, the maternal and fetal circulations are brought in close proximity to facilitate efficient exchange of various substances. (FIG. 1.)

As such, attempts have been made to study maternal-fetal transfer. (FIG. 2) However, such attempts have faced a variety of technical challenges. For example, in vivo animal models can be limited by interspecies differences and ex vivo perfusion of placental tissue is hampered by the limited length of time the tissue remains viable. While in vitro methods for studying maternal-fetal transport have been developed, e.g., culture of trophoblasts on semipermeable transwell supports, certain tissue culture platforms cannot be readily used for co-culture of two cell types and can be limited in their ability to recapitulate complex three-dimensional structure and dynamic mechanical and biochemical microenvironments that can play a role in health and disease.

Therefore, there is a need for a low-cost, human cell-based alternative to current maternal-fetal transfer models. Additionally, there is a need for a model that has improved parametric spatiotemporal control over the interaction of cells with their culture substrates, neighboring cells, and surrounding environment.

SUMMARY

The presently disclosed subject matter provides, in part, a microfluidic device that can simulate capillary blood flow in a fetal compartment of the device and pooled blood in a maternal compartment of the device (i.e., intervillous space). The microfluidic device can reconstitute the maternal-fetal interface, can expand the capabilities of cell culture models, and can provide an alternative to certain maternal-fetal transfer models.

In accordance with certain embodiments of the disclosed subject matter, a microfluidic device is provided. In certain embodiments, the microfluidic device comprises a base, a membrane, a first monolayer of cells of a first cell type and a second monolayer of cells of a second cell type. In certain embodiments, the base can have first and second microfluidic channels disposed thereon. In certain embodiments, the membrane can be disposed between the first and second microfluidic channels such that the first and second microfluidic channels are in fluid communication through the membrane. In certain embodiments, the membrane can have a first side and a second side. In certain embodiments, the first monolayer of cells of a first cell type can be disposed on the first side of the membrane. In certain embodiments, the second monolayer of cells of a second cell type can be disposed on the second side of the membrane. In certain embodiments, a first layer of a hydrogel can be formed on the first side of the membrane. In certain embodiments, a second layer of a hydrogel can be formed on the second side of the membrane. In certain embodiments, the first monolayer of cells of a first cell type can be disposed on the surface of the first hydrogel layer. In certain embodiments, the second monolayer of cells of a second cell type can be disposed on the surface of the second hydrogel layer. In certain embodiments, a second cell type can be encapsulated in the first or second hydrogel layer. In certain embodiments, a second cell type can be encapsulated in a hydrogel layer to induce three-dimensional vasculogenesis and vessel network formation. In certain embodiments, a third cell type can be encapsulated in the hydrogel layer.

In certain embodiments, the first cell type can be human umbilical vein endothelial cells ("HUVECs"). In certain embodiments, the first cell type can be primary human placental villous endothelial cells ("HPVECs"). In certain embodiments, the first cell type can be primary human endothelial cells isolated from the fetus. In certain embodiments, the first cell type can be transformed human endothelial cells derived from the fetus. In certain embodiments, the first cell type can be stem cell-derived endothelial cells. In certain embodiments, the second cell type can be choriocarcinoma (BeWo) cells. In certain embodiments, the second cell type can be BeWo b30 clone cells. In certain embodiments, the second cell type can be HTR8/SVneo trophoblast cells. In certain embodiments, the second cell type can be choriocarcinoma (JEG3) cells. In certain embodiments, the second cell type can be primary human trophoblasts. In certain embodiments, the second cell type can be stem cell-derived trophoblasts. In certain embodiments, the second cell type can be transformed human trophoblasts. In certain embodiments, the third cell type can be fibroblasts. In certain embodiments, the third cell type can be Hofbauer cells. In certain embodiments, the first, second, and/or third cell type can be animal cells. In certain embodiments, the first or second monolayer of cells can include an artificially or naturally induced pathology. In certain embodiments, the third cell type can include an artificially or naturally induced pathology. In certain embodiments, the naturally induced pathology can be from diseased placenta. In certain embodiments, the first or second monolayer of cells can include white blood cells.

In certain embodiments, the membrane can be a porous polycarbonate membrane. In certain embodiments, the pores can be 1 µm pores. In certain embodiments, the membrane can be one of a polyester membrane, a polytetrafluoroethylene membrane, an elastomeric (e.g., poly(dimethylsiloxane) (PDMS), polyurethane) membrane, a paper membrane, or an extracellular matrix membrane. In certain embodiments, the pores can have different sizes. In certain embodiments, the microfluidic device can include an additional layer of cells of a third type. In certain embodiments, the cross-sectional size of the microfluidic channel can be 500 µm (width)×100 µm (height). In certain embodiments, the cross-sectional size of the microfluidic channel can have different dimensions. In certain embodiments, the microfluidic device can include an additional layer made of a hydrogel (e.g., collagen gel) that contains other cell types. In certain embodiments, the other cell types can be cell types found in the stromal tissue between the trophoblasts epithelium and fetal endothelium, for example, fibroblasts and Hofbauer cells. In certain embodiments, endothelial cells can be embedded in the stromal tissue to form perfusable blood vessels.

In accordance with certain embodiments of the disclosed subject matter, a method of fabricating a microfluidic device is provided. In certain embodiments, the method can include fabricating a base. In certain embodiments, the base can have first and second microfluidic channels disposed thereon. In certain embodiments, the method can include disposing a membrane between the first and second microfluidic channels such that the first and second microfluidic channels are in fluid communication through the membrane. In certain embodiments, the membrane can have a first side and a second side. In certain embodiments, the method can include growing a first monolayer of cells of a first cell type disposed on the first side of the membrane, and growing a second monolayer of cells of a second cell type disposed on the second side of the membrane. In certain embodiments, a first layer of a hydrogel can be formed on the first side of the membrane. In certain embodiments, a second layer of a hydrogel can be formed on the second side of the membrane. In certain embodiments, the first monolayer of cells of a first cell type can be disposed on the surface of the first hydrogel layer. In certain embodiments, the second monolayer of cells of a second cell type can be disposed on the surface of the second hydrogel layer. In certain embodiments, a second cell type can be encapsulated in the first or second hydrogel layer. In certain embodiments, a second cell type can be encapsulated in a hydrogel layer to induce three-dimensional vasculogenesis and vessel network formation. In certain embodiments, a third cell type can be encapsulated in the hydrogel layer. In certain embodiments, additional layers of microchannels can be included to culture the other cell types derived from the placental stroma.

In certain embodiments, growing the first monolayer of cells can include placing (e.g., flowing) the cells of the first cell type on the first side of the membrane, creating a static environment to allow the cells to settle and attach to the membrane, and flowing a culture medium over the cells of the first cell type. In certain embodiments, growing the second monolayer of cells can include placing (e.g., flowing) the cells of the second cell type on the second side of the membrane, creating a static environment to allow the cells to settle and attach to the membrane, and flowing a culture medium over the cells of the second cell type. In certain embodiments, cell culture is maintained by placing the microfluidic device in a cell culture incubator. In certain embodiments, the microfluidic device can be maintained at different levels of oxygen. In certain embodiments, the microfluidic device can be operated at different flow rates to vary the hydrodynamic environment in the cell culture channels.

In accordance with certain embodiments of the disclosed subject matter, a method of testing placental maternal-fetal transfer is provided. In certain embodiments, the method can include providing a microfluidic device, as described hereinabove. In certain embodiments, the method can include placing a substance of interest in one of the first or second microfluidic channels. In certain embodiments, the method can include simulating physiological or pathological flow conditions. In certain embodiments, the method can include measuring the amount of the substance of interest in the other of the first and second microfluidic channel.

In certain embodiments, the substance of interest can be one of glucose, amino acids, proteins, immunoglobulins, antibodies, peptides, oxygen, carbon dioxide, nucleic acids, nanoparticulates, pathogens, environmental toxins, or pharmaceuticals. In certain embodiments, the substance of interest can be labeled with molecular probes (e.g., fluorophores), and measuring the amount of the substance of interest can include detecting the probes (e.g., fluorescence imaging).

BRIEF DESCRIPTION OF THE DRAWINGS

FIG. 1A provides a schematic of a human fetus and placenta within the uterine cavity. FIG. 1B provides a cross-sectional view of the placenta illustrating the placental cotyledons. FIG. 1C provides a diagram showing the maternal intervillous space separated from the lumen of the fetal capillary.

FIGS. 8A-8F illustrate the microengineered placental barrier in accordance with the disclosed subject matter. FIG. 8A provides an image showing a three-dimensional rendering of the microengineered placental barrier. FIG. 8B provides a cross-sectional view of the microengineered barrier. FIG. 8C provides an image illustrating trophoblast cells form a continuous network of epithelial adherens junctions. FIG. 8D provides an image showing cell-cell junctions of the placental villous endothelium. FIG. 8E shows trophoblast cells which produce laminin during culture in the disclosed microdevice. FIG. 8F provides a cross-sectional view of laminin deposition.

FIG. 9A provides a diagram showing a process of forming a multinucleated syncytiotrophoblast. FIG. 9B shows trophoblast cells cultured in the disclosed device. FIG. 9C provides a plot illustrating the permeability of the microengineered barrier to dextran during forskolin-induced syncytialization. FIG. 9D provides graphs showing β-human chorionic gonadotropin levels of trophoblast cells.

FIGS. 10A-10E illustrate glucose transport across the microengineered placental barrier in accordance with the disclosed subject matter. FIG. 10A provides an image showing syncytial epithelium in the disclosed device. FIG. 10B provides a cross-sectional view of the trophoblasts. FIG. 10C provides graphs showing immunofluorescence staining levels of $GLUT^1$. FIG. 10D provides a schematic illustrating a concentration gradient of glucose generated across the microengineered placental barrier. FIG. 10E provides graphs showing increases in fetal glucose concentration for the bare membrane, trophoblast monoculture, and co-culture conditions.

DETAILED DESCRIPTION

Figure 1:
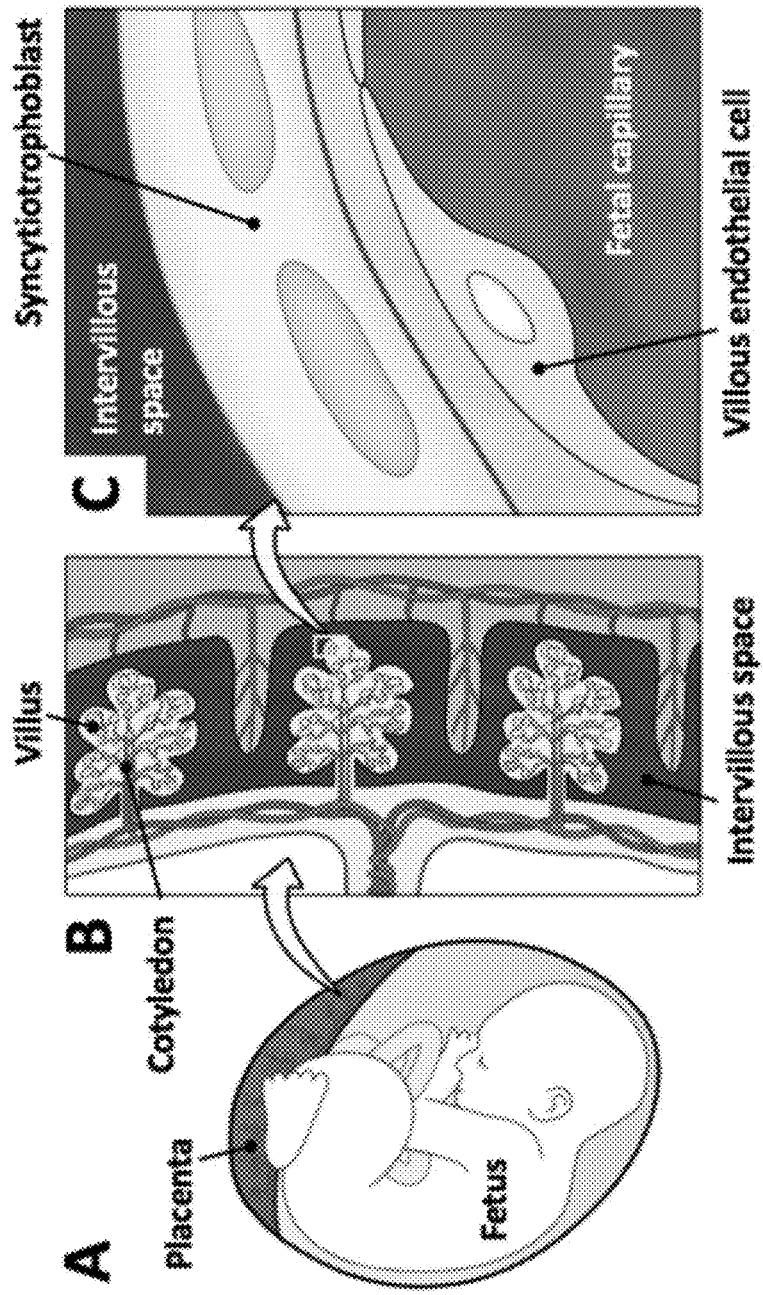
FIGS. 1A-1C illustrate the maternal-fetal interface of third trimester placenta.
Figure 2:
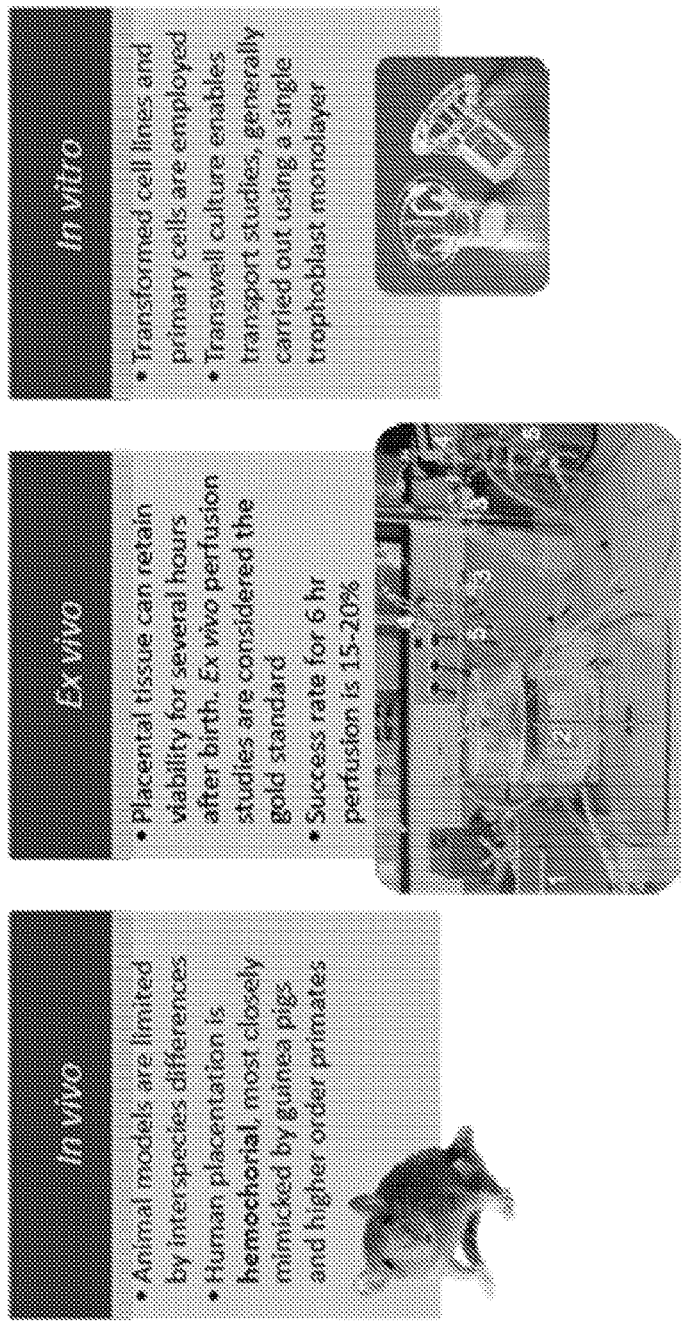
FIG. 2 illustrates alternative methods for maternal-fetal transfer research.
Figure 3:
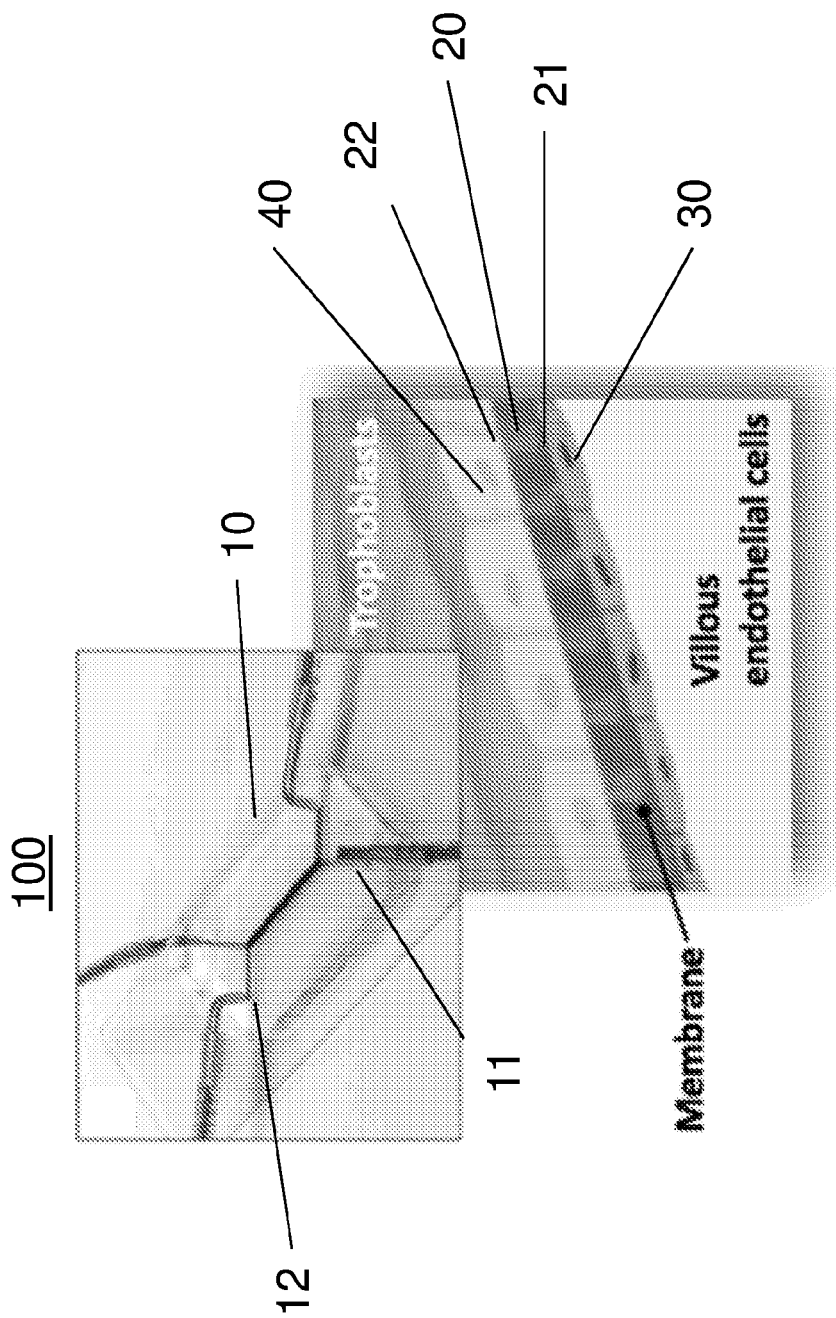
FIG. 3 provides an example microfluidic device in accordance with the disclosed subject matter.

The subject matter disclosed herein can leverage various microengineering technologies to develop a microengineered cell culture platform capable of reconstituting the three-dimensional microarchitecture, dynamic microenvironment, and physiological function of the placental barrier. In certain embodiments, the microfluidic device disclosed herein can allow for compartmentalized co-culture of human trophoblasts and endothelial cells in apposition on a thin, semipermeable polymeric membrane. In certain embodiments, the microfluidic device can enable compartmentalized co-culture of human trophoblasts, placental villous endothelial cells, stromal cells, immune cells, microbial cells, and viruses. In certain embodiments, physiological flow conditions can be simulated in the system to mimic capillary blood flow on the fetal side and convective motion of pooled blood on the maternal side. In certain embodiments, the flow conditions can be varied to mimic abnormal hemodynamic environment of the intervillous space and fetal capillaries. With reference to FIG. 3 for the purpose of illustration and not limitation, there is provided an exemplary microfluidic device 100. In certain embodiments, the microfluidic device 100 can include a base 10, a membrane 20, a first monolayer of cells 30, and a second monolayer of cells 40.

Figure 4:
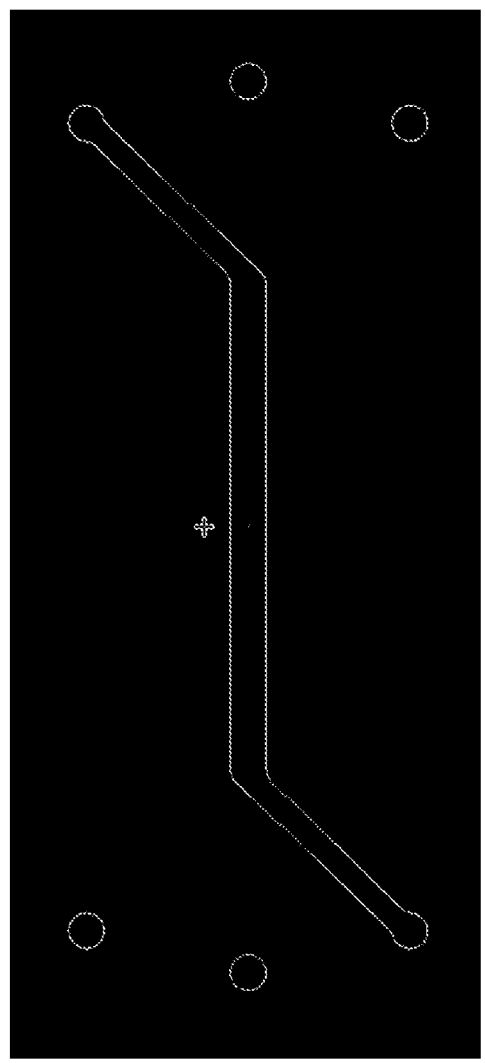
FIG. 4 illustrates a schematic of an example microfluidic channel design used for the microfluidic device in accordance with the disclosed subject matter.

In certain embodiments, the base 10 can include a first 11 and second 12 microfluidic channels disposed thereon. In certain embodiments, the first 11 or second 12 microfluidic channel can have the schematic design shown in FIG. 4. The microfluidic channels can have any suitable dimensions. For example, in certain embodiments, the cross-sectional size of the microfluidic channels can be 500 µm (width)×100 µm (height). In certain embodiments, the cross-sectional size of the microfluidic channels can be 1 mm (width)×135 µm (height). In certain embodiments, the microfluidic channels can be 1.5 cm in length. In certain embodiments, the cross-sectional size of the microfluidic channel can have different dimensions.

In certain embodiments, the base 10 can include additional channels (e.g., four, six, eight, or more, total channels) in pairs of two disposed thereon, with each pair having a membrane disposed therebetween (as discussed in further detail below). In certain embodiments, the base 10 can include channels in sets larger than two (e.g., three, four, or more) such that each of the channels in the set is separated from adjacent channels by a membrane. In certain embodiments, the base 10 can include one or more channels that are not adjacent to another channel, or separated from another channel by a membrane. The number of channels and layouts of the channels, including shape and dimensions, can vary based on the design of the base 10 and the experimental intent. In certain embodiments, each channel will have generally similar dimensions. In certain embodiments, the channels will have different dimensions. In certain embodiments, the base and microfluidic channels can be made of any suitable material, for example and without limitation, glass, metal, alloy, plastic, wood, paper, and polymer. In certain embodiments, the base and microfluidic channels can be made of poly(dimethylsiloxane) (PDMS).

In certain embodiments, the membrane 20 can be disposed between the first 11 and second 12 microfluidic channels such that the first 11 and second 12 microfluidic channels are in fluid communication through the membrane 20. In certain embodiments, the membrane 20 can have a first side 21 and a second side 22. In certain embodiments, the membrane 20 can be a thin polycarbonate membrane and can have 1 µm pores. In certain embodiments, the pores can be any suitable size. In certain embodiments, the pores can have varying pore sizes. In certain embodiments, the membrane can include porous portions and non-porous portions. In certain embodiments, the membrane 20 can be a polycarbonate membrane, a polyester membrane, a polytetrafluoroethylene membrane, an elastomeric membrane, a paper membrane, an extracellular matrix membrane, or any other suitable membrane. The selection of the pore sizes, materials and other features of the membrane can be varied based on the design of the microfluidic device, the experimental goals, or other suitable motivations.

Figure 5:
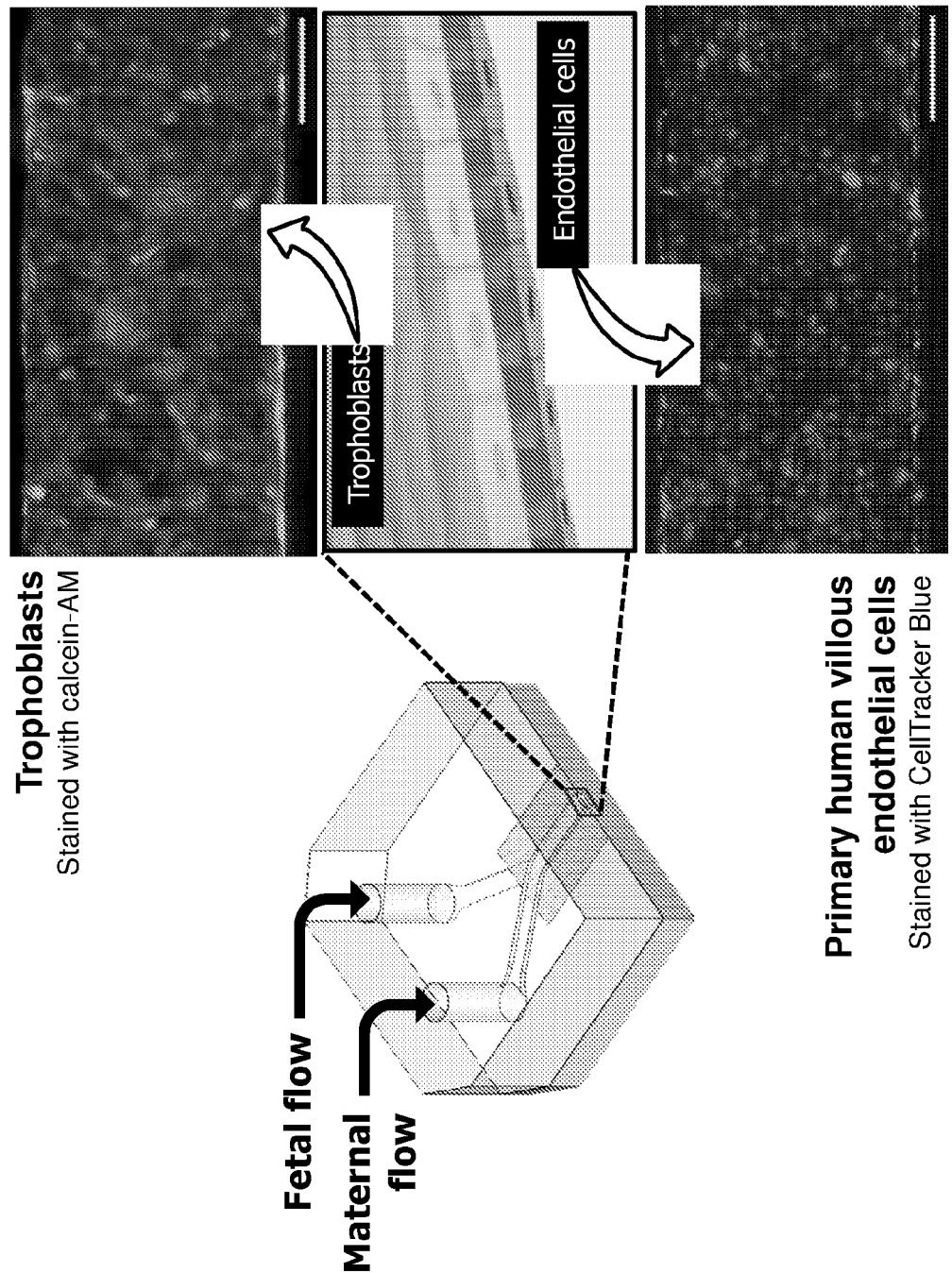
FIG. 5 illustrates a microfluidic device wherein BeWo cells are fluorescently stained with calcein AM and human placental villous endothelial cells are stained with CellTracker Blue.

In certain embodiments, appropriate cells can be introduced into the microfluidic channels. In certain embodiments, the first monolayer of cells 30 of a first cell type can be disposed on the first side 21 of the membrane. In certain embodiments, the second monolayer 40 of cells of a second cell type can be disposed on the second side 22 of the membrane. In certain embodiments, the first monolayer of cells 30 can be human placental villous endothelial cells ("HPVECs"). In certain embodiments, the second monolayer of cells 40 can be transformed choriocarcinoma (BeWo) cells. In certain embodiments, the first monolayer 30 and second monolayer 40 can be cultured in apposition on a membrane 20, as shown in FIG. 5. In certain embodiments, the first cell type can be human umbilical vein endothelial cells. In certain embodiments, the first cell type can be primary human endothelial cells isolated from the fetus. In certain embodiments, the first cell type can be transformed human endothelial cells derived from the fetus. In certain embodiments, the first cell type can be stem cell-derived endothelial cells. In certain embodiments, the second cell type can be choriocarcinoma (BeWo) cells. In certain embodiments, the second cell type can be BeWo b30 clone cells. In certain embodiments, the b30 clone can form a confluent monolayer and can be induced to differentiate into syncytial structure in the presence of cyclic AMP or forskolin. Syncytialized BeWo cells can provide a model of the syncytiotrophoblasts of in vivo terminal chorionic villi. In certain embodiments, the second cell type can be HTR8/SVneo trophoblast cells. In certain embodiments, the second cell type can be choriocarcinoma (JEG3) cells. In certain embodiments, the second cell type can be primary human trophoblasts. In certain embodiments, the second cell type can be stem cell-derived trophoblasts. In certain embodiments, the second cell type can be transformed human trophoblasts. In certain embodiments, alternative cell types can be used for the first or second monolayer, for example, primary villous trophoblasts or primary villous capillary endothelial cells harvested from term human placentas. In certain embodiments, primary villous trophoblasts or primary villous capillary endothelial cells can be harvested from preterm human placentas. In certain embodiments, animal cells can be used. Additionally, in certain embodiments, pregnancy-associated pathological conditions can be modeled using primary cells harvested from placentas of patients with complicated pregnancies (e.g. gestational diabetes, preeclampsia, intrauterine growth restriction). In certain embodiments, additional cell types can be added to the first or second monolayer, for example, placental fibroblasts, blood-borne immune cells, resident immune cells, or pathogenic cells. In certain embodiments, the additional cell types can be cell types found in the stromal tissue between the trophoblasts epithelium and fetal endothelium, for example, Hofbauer cells. In certain embodiments, endothelial cells can be embedded in the stromal tissue to form perfusable blood vessels. In certain embodiments, the structure of the first or second monolayer can be modified by adding three-dimensional gel layers. In certain embodiments, the first or second monolayer can have an artificially induced pathology.

In certain embodiments, an additional layer can be added to the microfluidic device 100, which can mimic the placenta during various stages of pregnancy. For example, in certain embodiments, a cell-laden hydrogel layer can be added to the microfluidic device 100 to mimic the thicker stroma layer of the maternal-fetal interface during the first trimester.

Figure 6:
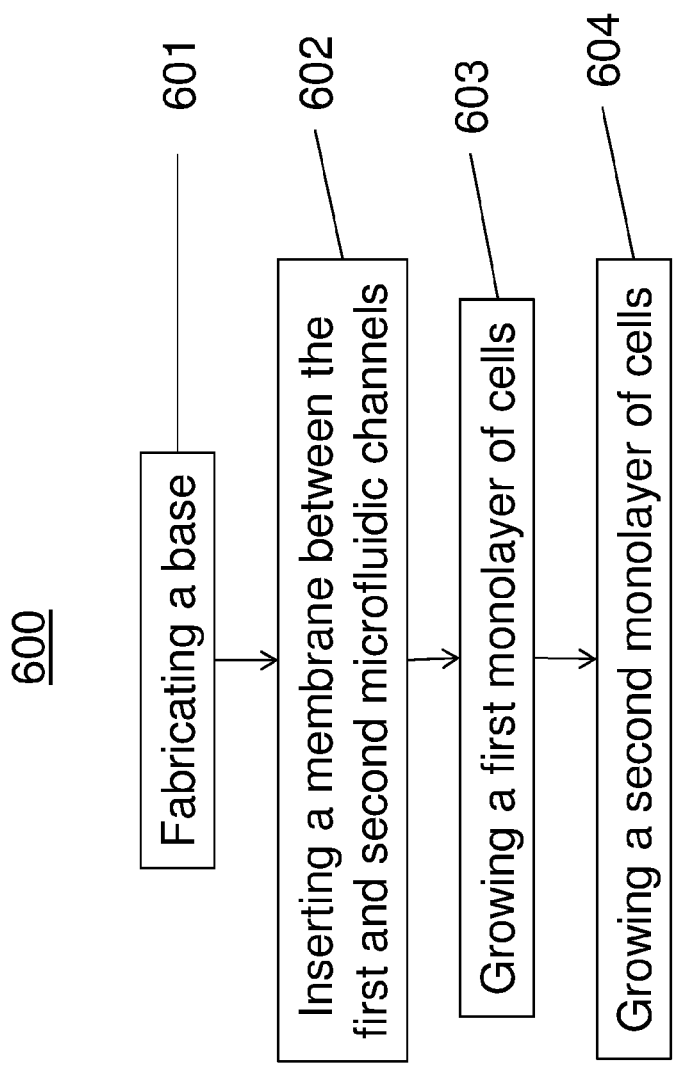
FIG. 6 provides an example method of fabricating a microfluidic device in accordance with the disclosed subject matter.

Referring to FIG. 6 for the purpose of illustration and not limitation, there is provided an exemplary method for fabricating a microfluidic device (600). In certain embodiments, the method can include fabricating a base (601), the base having first and second microfluidic channels disposed thereon. The base, including the microfluidic channels, can be built by any methods known in the art, including, but not limited to, those outlined in Huh et al., Nature Protocols 8:2135-2157 (2013). In certain embodiments, the method can include disposing a membrane between the first and second microfluidic channels (602) such that the first and second microfluidic channels are in fluid communication through the membrane. The membrane can have a first and second side. In certain embodiments, the method can include growing a first monolayer of cells (603) of a first cell type disposed on a first side of the membrane, and growing a second monolayer of cells (604) of a second cell type disposed on a second side of the membrane.

In certain embodiments, a first layer of a hydrogel can be formed on the first side of the membrane. In certain embodiments, a second layer of a hydrogel can be formed on the second side of the membrane. In certain embodiments, the first monolayer of cells of a first cell type can be disposed on the surface of the first hydrogel layer. In certain embodiments, the second monolayer of cells of a second cell type can be disposed on the surface of the second hydrogel layer. In certain embodiments, a second cell type can be encapsulated in the first or second hydrogel layer. In certain embodiments, a second cell type can be encapsulated in a hydrogel layer to induce three-dimensional vasculogenesis and vessel network formation. In certain embodiments, a third cell type can be encapsulated in the hydrogel layer. In certain embodiments, additional layers of microchannels can be included to culture other cell types derived from the placental stroma.

In certain embodiments, the membrane is coated with extracellular matrix protein for optimal cell adhesion. In certain embodiments, the membrane can be coated with extracellular matrix by filling and incubating the microfluidic channels in a human fibronectin solution. In certain embodiments, growing the first monolayer can include placing, e.g., flowing, cells of the first cell type on the first side of the membrane. In certain embodiments, a static environment can be created to allow the cells to settle and attached to the membrane. In certain embodiments, the method can include flowing a culture medium over the cells. In certain embodiments, growing the second monolayer can include similar steps. In certain embodiments, the entire microfluidic device can be placed in a cell culture incubator for maintenance of cell culture. In certain embodiments, the microfluidic device can be maintained at different levels of oxygen. In certain embodiments, the microfluidic device can be operated at different flow rates to vary the hydrodynamic environment in the cell culture channels.

Figure 7:
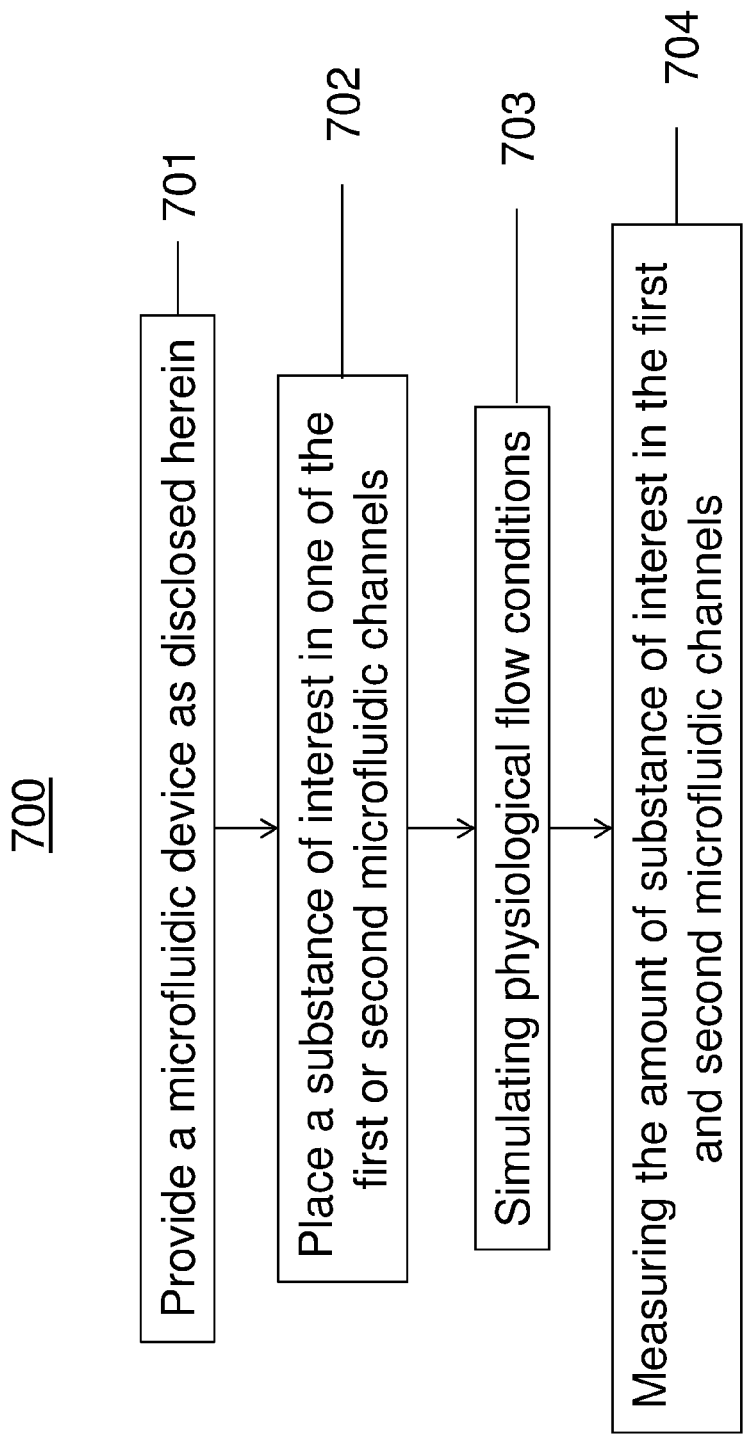
FIG. 7 provides an example method of testing placental maternal-fetal transfer in accordance with the disclosed subject matter.

Referring to FIG. 7 for the purpose of illustration and not limitation, an exemplary method of testing metabolic regulation of a placenta (700) is provided. In certain embodiments, the method can include providing a microfluidic device (701) as disclosed herein, and can include placing a substance of interest in one of the first or second microfluidic channels (702). In certain embodiments, the substance of interest can be, for example, glucose, amino acids, proteins, immunoglobulins, antibodies, peptides, oxygen, carbon dioxide, nucleic acids, nanoparticulates, pathogens, environmental toxins, or other suitable substances, e.g., pharmaceuticals. In certain embodiments, the method can include simulating physiological or pathological flow conditions (703). For example, in certain embodiments, the system can mimic capillary blood flow on the fetal side and convective motion of pooled blood on the maternal side. In certain embodiments, the method can include measuring the amount of a substance of interest in the first and second microfluidic channels (704). In certain embodiments, the substance can be measured for example by a glucometer if the substance of interest is glucose. In certain embodiments, the substance of interest can be labeled with a fluorescent reporter, and the amount of substance can be measured by measuring an amount of fluorescence, for example, by placing the fluid output into a plate reader for fluorescence detection. In certain embodiments, the substance of interest can be labeled in other manners, for example, radiolabeling or other biochemical labeling methods. In certain embodiments, the percent rate of transfer of the substance of interest can be calculated using the following equation:

$$\% \text{ rate of transfer} = \frac{\Delta C_F}{\Delta C_M} \times 100 \qquad (1)$$

where $\Delta C_F$ and $\Delta C_M$ denote changes in the concentrations of the substance of interest in the microfluidic channels of the fetal and maternal sides during perfusion, respectively.

In certain embodiments, the microfluidic device can include additional elements, for example, integrated pumps, valves, bubble traps, oxygenators, gas-exchangers, in-line microanalytical functions, and other suitable elements. Such elements can allow for additional control and experimentation using the device. In certain embodiments, the microfluidic device can include features for automatically performing experiments on the device. For example, in some embodiment, the microfluidic device can include automated valve or fluid control mechanisms or automatic testing mechanisms, such as sensors or monitors. In certain embodiments, the microfluidic device can be maintained in a hypoxic cell culture environment to mimic early gestational physiology. Alternatively or additionally, in certain embodiments, the microfluidic device can be configured to be coupled with other sensors or monitors not disclosed on the device. In certain embodiments, the microfluidic device can include a cleaning reservoir coupled to the channels for cleaning or sterilizing the channels. In certain embodiments, the microfluidic device can be modular in construction, thereby allowing various elements to be attached or unattached as necessary during various cleaning, experimenting, and imaging processes. In certain embodiments, the microfluidic device, or portions thereof, can be reusable, and in some embodiments, the microfluidic device, or portions thereof, can be disposable.

In certain embodiments, the microfluidic device disclosed herein can be used to study placental exchange of various endogenous and exogenous substances such as oxygen, nutrients, metabolic waste, and xenobiotics. Furthermore, in certain embodiments, the microfluidic device disclosed herein can provide opportunities to develop specialized human disease models that can use patient-derived cells to simulate complex human-specific disease processes for a variety of biomedical, pharmaceutical, toxicological, and environmental applications. For example, in certain embodiments, the microfluidic device disclosed herein can be used to study placental pathologies as well as the metabolic regulation of inflammatory pathways and other pathophysiologic processes that can occur in the placenta. Additionally, in certain embodiments, the microfluidic device disclosed herein can be used as a screening tool to evaluate the safety and toxicity of environmental exposures (e.g., chemicals, toxins) and drugs during pregnancy, and the drug transfer between the maternal and fetal circulations. Furthermore, in certain embodiments, by including additional tissue layers that can mimic the placental villous stroma, the microfluidic device disclosed herein can be used to study placental biology and physiology at different stages of gestation.

The following example is merely illustrative of the presently disclosed subject matter and should not be considered as a limitation in any way.

EXAMPLE

The microfluidic device of presently disclosed subject matter can be fabricated using standard soft lithography techniques. For examples, the base can be constructed with an upper layer and a lower layer made of Polydimethylsiloxane (PDMS) (Sylgard, Dow Corning), each layer containing a microfluidic channel. PDMS base can be mixed with curing agent at a weight ratio of 10:1 and degassed to remove air bubbles. The mixture can be cast on a silicon master containing photolithographically prepared microchannel features of SU-8 (MicroChem). The microfluidic channels can be 1 mm (width)×1.5 cm (length)×135 um (height). A biopsy punch can be used to create 1 mm-diameter holes through the upper PDMS slab to gain fluidic access to the microfluidic channels.

The microfluidic device can be assembled by bonding the two PDMS layers to a semipermeable polycarbonate membrane containing 1 μm pores (GE Healthcare) using adhesive PDMS mortar. To create the mortar film, PDMS precursors can be mixed with a curing agent at a weight ratio of 10:3 and spin-coated on a 100 mm Petri dish at 2500 rpm for 5 minutes. Subsequently, both the upper and lower layers of the microfluidic device can be gently placed on the dish to transfer the spin-coated mortar film onto the surfaces of the PDMS slabs containing the microchannel features. This step can be followed by bonding of the polycarbonate membrane to the upper PDMS slab. These two layers can then be aligned and attached to the lower PDMS slab, and cured at room temperature overnight to ensure complete bonding.

The BeWo b30 human trophoblast cell line can be cultured in DMEM/F-12K medium (GE Healthcare) containing 10% fetal bovine serum (FBS), 1% L-glutamine, and 1% penicillin/streptomycin (Gibco). Human primary placental villous endothelial cells (HPVECs) can be isolated from term placentas and maintained in EGM-2 medium containing 2% FBS (Lonza).

The assembled microfluidic device can be first sterilized using UV irradiation. Following sterilization, the surface of the intervening porous membrane can be coated with extracellular matrix (ECM) by filling and incubating the microchannels with a human fibronectin solution (0.1 mg/ml in phosphate buffered saline (PBS)) at 37° C. for 4 hours. The channels can then be rinsed with PBS to remove the ECM solution prior to cell seeding.

To form the fetal endothelium, a suspension of trypsinized HPVECs ($4 \times 10^6$ cells/ml) can be introduced into the lower microchannel and the device can then be inverted to allow the cells to settle to the original lower side of the porous membrane. Subsequently, the seeded microfluidic device can be incubated at 37° C. for 1 hour to enable cell attachment and spreading. During this period, the inlet and outlet access ports can be blocked to prevent unwanted convective motion of culture medium in the microchannels.

After the attachment of HPVECs is confirmed, the device can be flipped back, and the upper microchannel can be seeded with BeWo cells suspended in DMEM/F-12K at a concentration of 4×106 cells/ml. After incubation at 37° C. for 1 hour, the microfluidic device can be connected to syringe pumps that generated continuous flow of culture media in the upper and lower microchannels at a volumetric flow rate of 100 μL/hr.

The trophoblast and endothelial cell populations introduced into the microchannels can establish firm adhesion to the ECM-coated membrane and begin to spread within a few hours of cell seeding. During perfusion culture, these cells can proliferate in a continuous manner to form confluent monolayers in both the upper and lower chambers, which can cover the surface of the membrane within 24 hours of initial cell seeding. FIG. 8A provides a three-dimensional rendering of the immunofluorescence image of the engineered bi-layer tissue. FIG. 8B provides a cross-sectional view of the same tissue. The resulting bi-layer tissue can closely resemble the trophoblast-endothelial interface of the chorionic villus in vivo. Despite porosity of the interstitial membrane, cell transmigration does not appear to occur between the microchannels. This can be due to the small size of the membrane pores (e.g. 1 μm). Under perfusion culture conditions, the microengineered placental barrier can be maintained without a significant loss of cell viability for prolonged periods (e.g. >1 week).

Formation of cell-cell junctions can be evaluated to assess structural integrity of the barrier. In order to assess the formation of intercellular junctions, the trophoblast cells and HPVECs can be fixed in 4% paraformaldehyde (PFA) for 15 minutes, permeabilized in 0.25% Triton X-100 for 10 minutes, and then incubated in 2% bovine serum albumin (BSA) for 1 hour. All steps can be performed at room temperature. The trophoblast cells and HPVECs can be incubated with anti-E-cadherin (Life Technologies) and anti-VE-cadherin antibodies (Cell Signaling Technologies), respectively. These primary antibodies can be diluted in 2% BSA and incubated in the microfluidic device for 1 hour at room temperature. Next, the samples can be thoroughly washed with PBS. Secondary antibodies (Life Technologies) can be diluted in 2% BSA, incubated for 45 minutes at room temperature, and then washed with PBS. Nuclei can be labeled using DAPI subsequent to the secondary antibody incubation. Following staining, the membrane can be removed from the microfluidic device and mounted onto a coverslip. Images can be acquired using an inverted microscope (Zeiss Axio Observer) and a confocal laser-scanning microscope (Leica TCS SP8). Image processing and three-dimensional rendering can be carried out using Volocity (PerkinElmer).

VE-cadherin expression in the fetal endothelium and E-cadherin in the trophoblast cells can be visualized hereby. Immunofluorescence imaging of the bilayer tissue cultured for 3 days can show a network of continuous and defined junctional complexes throughout both the trophoblast and endothelial layers. FIG. 8C shows an immunofluorescence image of the trophoblast cells that form a continuous network of epithelial adherens junctions. The E-cadherin 801 is shown in red and nuclei 802 are stained with DAPI (blue). FIG. 8D further illustrates that the placental villous endothelium can also display intact cell-cell junctions (VE-cadherin 803, red). Green and blue show actin 804 and nuclear 805 staining, respectively. Expression of the junctional proteins can be uniform across the cell culture membrane, showing no indication of localized regions with immature junctions. Considering that intercellular adhesion plays a role in placental transport in vivo, these results demonstrate the capability of the disclosed subject matter to recapitulate not only the relative spatial arrangement of the maternal and fetal tissue in the placental barrier but also structural integrity necessary for its function.

Microfluorimetric analysis of the placental barrier in the microfluidic device can also reveal evidence of extracellular matrix remodeling by trophoblast cells. In the human placenta, laminin is a component of the trophoblast basement membrane in the chorionic villus that contributes to barrier integrity. Confocal microscopy of the trophoblast cells cultured in the microfluidic device for 6 days can show extensive extracellular deposition of laminin (FIG. 8E, showing laminin 806 in green). Moreover, this deposition can be localized to the basal side of the cells, forming a thin layer of laminin between the epithelium and underlying semipermeable membrane 807 (FIG. 8F, showing a cross sectional view), which is reminiscent of the basal lamina in vivo.

Following the formation of a confluent epithelial monolayer on the membrane surface in the upper microchannel, the apical side of the epithelium can be treated with forskolin to activate the protein kinase A pathway in the cultured trophoblasts. A stock solution of forskolin (Sigmal 5 mg/mL in DMSO) can be diluted with F-12K medium to a final concentration of 50 uM and perfused through the upper microchannel. After 72 hours of forskolin treatment, the trophoblast cells can be fixed in 4% PFA, permeabilized in Triton-X 100, and then incubated with 2% BSA in PBS for immunofluorescence staining. To analyze changes in junctional protein expression, the samples can be incubated with anti-E-cadherin antibody (Life Technologies) in 2% BSA, followed by secondary antibody and DAPI. Additionally, media perfusate can be collected at 48, 72, and 96 hours from both untreated and forskolin-treated devices. The collected samples can be analyzed using a human chorionic gonadotropin beta ($\beta$-hCG) ELISA kit (Abcam) to quantify the levels of $\beta$-hCG produced by the trophoblast population at each time point.

Barrier function of the syncytialized epithelium can be assessed by measuring the transport of 3 kDa fluorescein isothiocyanate-dextran (FITC-dextranl Life Technologies) between the maternal and fetal compartments. FITC-dextran (0.1 mg/mL in DMEM/F-12K media) can be introduced to the upper maternal microchannel and perfused for 3 hours. The media perfusate can be collected from both microchannels during this period and the fluorescence intensity of the collected samples can be quantified using a microplate reader (Tecan). The amount of dextran transport can be assessed based on the mean fluorescence intensity in the outflow from the lower fetal microchannel.

Figure 9A:
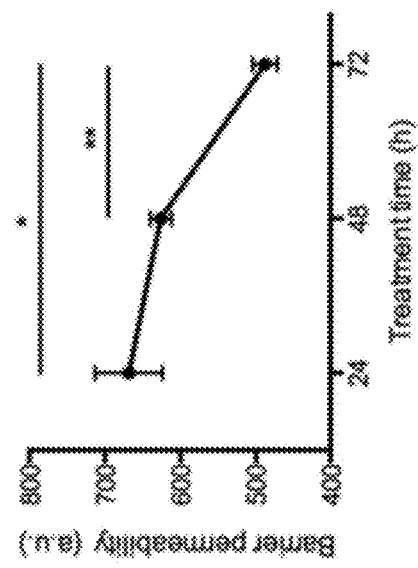
FIGS. 9A-9D illustrate trophoblast syncytialization.

With the progression of pregnancy, cytotrophoblast cells covering the chorionic villi of the human placenta can differentiate and fuse to form a multinucleated syncytiotrophoblast (FIG. 9A). This terminally differentiated syncytium forms the continuous outer lining of the chorionic villi and comes in direct contact with maternal blood in the intervillous space. This process of syncytialization can be a hallmark of placentation and play a role in physiological function of the placental barrier as a regulator of material exchange between the maternal and fetal circulations. While the underlying molecular pathways of syncytialization are not fully understood, it is known that activation of adenylate cyclase, which is the regulatory subunit of protein kinase A, by 3',5'-cyclic monophosphate (cAMP) or forskolin induces BeWo cells and primary villous cytotrophoblast cells to fuse and acquire differentiated phenotypes of the syncytiotrophoblast.

Figure 9B:
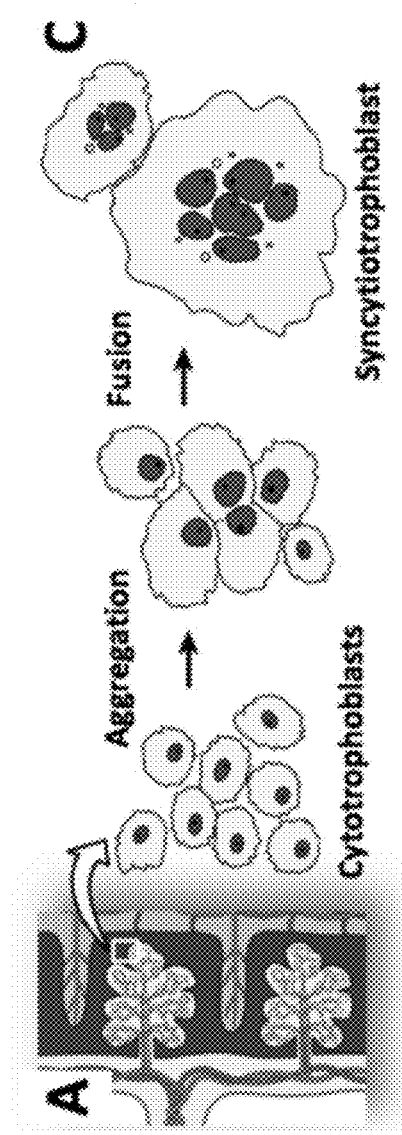
Figure 9C:
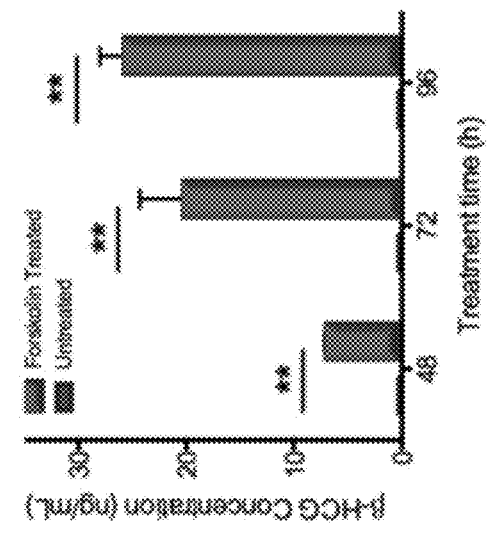

Accordingly, when the BeWo cells in the maternal compartment are exposed to forskolin, they can begin to undergo cell-cell fusion as illustrated by nuclear aggregation that can be evident at 72 hours of forskolin treatment (FIG. 9B). This response can occur in approximately 50% of the BeWo population and does not necessarily exert deleterious effects on cell viability. Concurrent to the fusion of trophoblast cells can be a loss of epithelial cell-cell junctions. The microscopic inspection of the trophoblasts can show downregulation of E-cadherin throughout the epithelial layer (FIG. 9B). This reduced expression of junctional proteins does not necessarily compromise the structural integrity of the barrier. On the contrary, syncytialization in the disclosed subject matter can lead to improved barrier function. When paracellular permeability is measured using FITC-dextran, the amount of dextran transport across the barrier can decrease over the course of forskolin exposure (FIG. 9C). These observations can match characteristic alterations in the morphology and barrier function of BeWo cells during their acquisition of syncytiotrophoblast-like phenotypes, indicating successful syncytialization of the trophoblast epithelium in the disclosed subject matter.

Figure 9D:
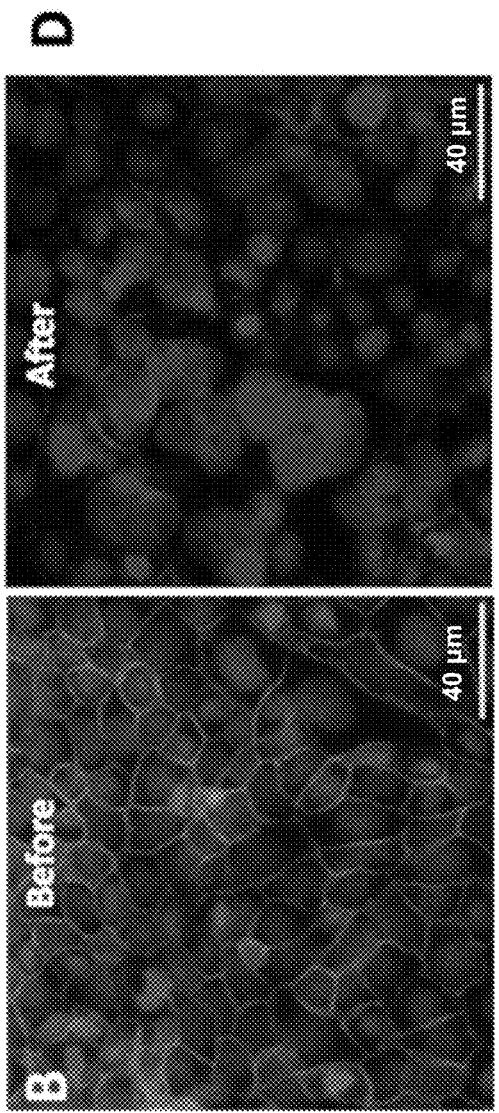

A functional consequence of trophoblast syncytialization in the human placenta is the production of hormones that play a role in the progression of both placental and fetal development. As a representative example of a placental hormone, human chorionic gonadotropin (hCG) can be secreted by the syncytiotrophoblast and serve as a biochemical marker of in vitro trophoblast differentiation. Accordingly, the production of the $\beta$ subunit of hCG in the maternal compartment can be measured to quantitatively examine syncytialization. In the absence of forskolin, analysis of maternal outflow does not necessarily yield detectable $\beta$-hCG (FIG. 9D). In contrast, administration of forskolin can trigger production of hCG by trophoblast cells within 48 hours, and the hormone levels can continue to increase over the course of 96 hours of forskolin treatment (FIG. 9D). The extent of increase can be greater in the first 48 hours, implying positive feedback control of cell differentiation during the initial period of stimulation. This can be explained by the known phenomenon that hCG produced by differentiated trophoblast cells can activate adenylyl cyclase to increase intracellular cAMP and thus to further promote trophoblast differentiation. The above results demonstrate that the presently disclosed subject matter can enable both morphological and functional differentiation of trophoblast cells to reconstitute the syncytium of the placental barrier.

In order to evaluate the presence and spatial distribution of glucose transporters in the microengineered placental barrier, cells, after 3 days of microfluidic culture, can be processed for immunofluorescence imaging as described above. Briefly, cells can be fixed on-chip in 4% PFA, permeabilized in Triton-X 100, and incubated in 2% BSA in PBS. The samples can then be incubated with mouse anti-glucose transporter 1 antibody (Abcam), followed by secondary antibody (Life Technologies). Images can be acquired using a confocal laser-scanning microscope (Leica), and image processing can be carried out using Volocity software (PerkinElmer). Assessment of transporter membrane localization can be performed using FIJI. The apical and basal membranes can be manually segmented in 10 representative images, and the mean fluorescence intensity can be measured in each image. These values can be adjusted for background fluorescence.

To analyze glucose transport across the maternal-fetal interface, the maternal compartment can be perfused with culture medium containing 10 mM glucose. This increased glucose concentration can be generated by adding D-glucose (Gibco) to F-12K medium. Media on the fetal side can contain 5 mM of glucose during perfusion. Outflow from the maternal and fetal microchannels can be collected over a period of 2 hours and analyzed by a glucose meter (Accu-Chek Aviva) to measure glucose concentration. These studies can be carried out to measure the rate of transport across three types of barriers: (1) a bare membrane in a cell-free device, (2) a monolayer of BeWo trophoblasts without the endothelium, and (3) an epithelial-endothelial barrier formed by co-culture of BeWo trophoblast cells and HPVECs. For each group, barrier function can be quantified by the percent increase in fetal glucose concentration over the period of perfusion. Additionally, the percent rate of transfer can be calculated for the co-culture model using equation (1) as described above. This value can be compared to the percent rate of transfer measured in a human placenta to investigate the physiological relevance of the presently disclosed subject matter.

Glucose from the maternal circulation is a primary source of energy for fetal growth and development during pregnancy. The maternal-to-fetal transport of glucose across the placental barrier can be mediated by facilitated diffusion via a family of membrane-bound glucose transporters (GLUTs). GLUT1 is a type of glucose transporter in a human placenta and can be found in the syncytium of the placental barrier. Its expression is known to increase over the second half of pregnancy to meet the increased rate of fetal growth. While GLUT1 transporters can be expressed in both the apical and basolateral surfaces of the syncytiotrophoblast layer, they have asymmetric localization, with a greater proportion located on the apical microvillous membrane facing the maternal intervillous space. The disclosed subject matter can recapitulate this pattern of GLUT1 expression. Immunofluorescence analysis demonstrates expression of GLUT1 transporters in the population of differentiated trophoblast cells comprising the microengineered syncytium (FIG. 10A, showing GLUT1 transporters in red). Moreover, there can be increased GLUT1 expression on the apical side of the epithelium, resembling the native spatial distribution of the transporter (FIGS. 10B, 10C).

For the quantitative analysis of glucose transport in the disclosed system, facilitated diffusion of glucose from the maternal to fetal compartment can be induced by creating a concentration gradient across the microengineered tissue interface (FIG. 10D). Glucose transport in a microfluidic device consisting of the upper and lower microchannels separated by a bare membrane can serve as a control. Measurements taken from this acellular system can be used to establish the baseline permeability of the porous membrane to maternal glucose. To assess the contribution of the epithelium to barrier function, another control group can be generated by similar devices used for monoculture of trophoblasts in the maternal compartment. As shown in FIG. 10E, the presence of the epithelial barrier in this group can lead to approximately 50% reduction in the percent increase in fetal glucose concentration as compared to the baseline data obtained from the acellular model. When fetal endothelial cells are included to establish a co-culture model, permeability can decrease further due to the additional cell layer, and the increase in fetal glucose can be evaluated to be roughly 30% of that measured in the trophoblast monoculture group. These results can demonstrate the ability of the differentiated trophoblasts in the disclosed system to mediate glucose transport. It also indicates that the fetal endothelium can potentially have a previously underappreciated effect on the rate of glucose transport by providing an additional barrier to the facilitated diffusion.

The results reveal that the percent rate of glucose transfer from the maternal to the fetal compartments is 34.8%. This value lies within the range of glucose transfer rates measured in the perfused ex vivo human placenta (26.5-38.3%). This quantitative similarity can be advantageous, considering that animal data does not necessarily predict glucose transfer in the human placenta due to interspecies differences in the molecular underpinnings of transport function. For example, glucose transport in the murine and rodent placenta is mediated predominantly by GLUT3, whereas GLUT1 is the primary glucose transporter in the human placental barrier. Hence, the above results illustrate the feasibility of using the disclose system as an alternative to existing animal models to simulate physiological glucose transport across the intact human placental barrier.

It will be apparent to those skilled in the art that various modification and variations can be made in the structure and method of the disclosed subject matter without departing from the spirit or scope of the disclosed subject matter. Thus, it is intended that the disclosed subject matter include modifications and variations that are within the scope of the appended claims and their equivalents.

The invention claimed is:

1. A microfluidic device comprising:
   a base, having first and second microfluidic channels disposed thereon;
   a membrane disposed between the first and second microfluidic channels such that the first and second microfluidic channels are adapted for fluidic communication through the membrane, the membrane having a first side and a second side;
   a first monolayer of cells of a first cell type disposed on the first side of the membrane, wherein the first cell type comprises a primary human placental villous endothelial cell; and
   a second monolayer of cells of a second cell type disposed on the second side of the membrane.

2. The microfluidic device of claim 1, wherein the second cell type comprises choriocarcinoma cells.

3. The microfluidic device of claim 1, wherein the second cell type comprises choriocarcinoma b30 clone cells.

4. The microfluidic device of claim 3, wherein the second cell type is differentiated into syncytial structures.

5. The microfluidic device of claim 1, wherein one of the first or second monolayer of cells further comprises an artificially induced pathology.

6. The microfluidic device of claim 1, wherein the first or second monolayer of cells further comprises white blood cells.

7. The microfluidic device of claim 1, wherein the membrane comprise a porous polycarbonate membrane.

8. The microfluidic device of claim 1, wherein the membrane is coated with an extracellular matrix.

9. The microfluidic device of claim 7, wherein the membrane comprises 1 µm pores.

10. The microfluidic device of claim 1, wherein the membrane comprises one of a polyester membrane, a polytetrafluoroethylene membrane, a paper membrane, an elastomeric membrane, or an extracellular matrix membrane.

11. The microfluidic device of claim 1, further comprising an additional layer of cells of a third type.

12. A method of fabricating a microfluidic device comprising:
   fabricating a base, the base having first and second microfluidic channels disposed thereon;
   disposing a membrane between the first and second microfluidic channels such that the first and second microfluidic channels are adapted for fluidic communication through the membrane, the membrane having a first side and a second side;
   growing a first monolayer of cells of a first cell type disposed on the first side of the membrane, wherein the first cell type comprises a primary human placental villous endothelial cell; and
   growing a second monolayer of cells of a second cell type disposed on the second side of the membrane.

13. The method of claim 12, wherein growing a first monolayer of cells further comprises
   placing cells of the first cell type on the first side of the membrane;
   creating a static environment to allow the cells to settle and attach to the membrane; and
   flowing a culture medium over the cells of the first cell type.

14. The method of claim 12, wherein growing a second monolayer of cells further comprises
   placing cells of the second cell type on the second side of the membrane;
   creating a static environment to allow the cells to settle and attach to the membrane; and
   flowing a culture medium over the cells of the second cell type.

15. The method of claim 12, further comprising placing the microfluidic device in a cell culture incubator.

16. A method of testing placental maternal-fetal transfer, comprising
   providing a microfluidic device having:
      a base, having first and second microfluidic channels disposed thereon;
      a membrane disposed between the first and second microfluidic channels such that the first and second microfluidic channels are adapted for fluidic communication through the membrane, the membrane having a first side and a second side;
      a first monolayer of cells of a first cell type disposed on the first side of the membrane, wherein the first cell type comprises a primary human placental villous endothelial cell; and
      a second monolayer of cells of a second cell type disposed on the second side of the membrane;
   placing a substance of interest in one of the first or second microfluidic channels;
   simulating physiological flow conditions; and
   measuring the amount of the substance of interest in the first and second microfluidic channels.

17. The method of claim 16, wherein the substance of interest is one of glucose, amino acids, proteins, or small molecule pharmaceuticals.

18. The method of claim 16, wherein the substance of interest is labeled with fluorescent molecules, and wherein measuring the amount of substance of interest comprises measuring an amount of fluorescence.

* * * * *